(12) United States Patent
Sweeney et al.

(10) Patent No.: US 7,347,751 B2
(45) Date of Patent: Mar. 25, 2008

(54) CARDIAC LEAD IMPLANTATION SYSTEM

(75) Inventors: Robert J. Sweeney, Woodbury, MN (US); Ed J. Mikolajczyk, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 167 days.

(21) Appl. No.: 10/955,636

(22) Filed: Sep. 30, 2004

(65) Prior Publication Data

US 2006/0069419 A1    Mar. 30, 2006

(51) Int. Cl.
*A61N 1/05* (2006.01)

(52) U.S. Cl. .................. 439/909; 607/115; 607/116; 607/119; 607/122

(58) Field of Classification Search ........ 607/115–116, 607/119, 122; 439/909
See application file for complete search history.

(56) References Cited

U.S. PATENT DOCUMENTS

| | | | |
|---|---|---|---|
| 4,362,164 A | 12/1982 | Little et al. | |
| 4,674,518 A | 6/1987 | Salo | |
| 5,088,491 A | 2/1992 | Schaldach | |
| H1347 H | 8/1994 | Greeninger et al. | |
| 5,469,859 A | 11/1995 | Tsoglin et al. | |
| 5,741,214 A | 4/1998 | Ouchi et al. | |
| 5,944,746 A | 8/1999 | Kroll | |
| 6,021,350 A | 2/2000 | Mathson | |
| 6,171,263 B1 | 1/2001 | Sullivan | |
| 6,247,474 B1 | 6/2001 | Greeninger et al. | |
| 6,256,538 B1 | 7/2001 | Ekwall | |
| 6,263,246 B1 | 7/2001 | Goedeke et al. | |
| 6,264,606 B1 | 7/2001 | Ekwall et al. | |
| 6,331,703 B1 | 12/2001 | Yarnall et al. | |
| 6,535,763 B1* | 3/2003 | Hiebert et al. | 607/32 |
| 6,714,806 B2 | 3/2004 | Iaizzo et al. | |
| 2002/0046756 A1* | 4/2002 | Laizzo et al. | 128/899 |
| 2005/0177199 A1* | 8/2005 | Hansen et al. | 607/37 |

* cited by examiner

*Primary Examiner*—Carl Layno
*Assistant Examiner*—Deborah Malamud
(74) *Attorney, Agent, or Firm*—Hollingsworth & Funk, LLC

(57) ABSTRACT

Cardiac lead implantation systems and methods including an electronics arrangement provided with a user interface and a coupler assembly. A coupler body is configured to detachably grasp a cardiac lead and couple with electrical contacts of the cardiac lead. A user interface includes an output indicative of sensed cardiac parameters, such as one or both of cardiac signal amplitude and lead electrode impedance, and may include an audio output device and/or a visual output device. Methods of lead implantation involve advancing a cardiac lead into proximity with a patient's heart, and contacting cardiac tissue with an electrode arrangement to locate a suitable implant location. Sensing of one or more cardiac parameters is accomplished and an audible representation of the sensed parameters is produced, the audible representation varying as the electrode arrangement is moved relative to the cardiac tissue.

29 Claims, 7 Drawing Sheets

CARDIAC LEAD IMPLANTATION SYSTEM

FIELD OF THE INVENTION

The present invention relates generally to implantable medical devices and, more particularly, to a cardiac lead implantation system and method of lead implantation.

BACKGROUND OF THE INVENTION

Rhythmic contractions of a healthy heart are normally initiated by the sinoatrial (SA) node that includes specialized cells located in the superior right atrium. The SA node is the normal pacemaker of the heart, typically initiating 60-100 heartbeats per minute. When the SA node is pacing the heart normally, the heart is said to be in normal sinus rhythm (NSR).

The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways can suffer compromised cardiac output, such as that associated with congestive heart failure, for example.

Cardiac rhythm management devices have been developed that provide pacing stimulation to one or more heart chambers in an attempt to improve the rhythm and coordination of atrial and/or ventricular contractions. Cardiac rhythm management devices may also incorporate defibrillation circuitry used to treat patients with serious arrhythmias. Cardiac rhythm management devices typically include circuitry to sense signals from the heart and a pulse generator for providing electrical stimulation to the heart. One or more leads are typically delivered transveneoulsy into the heart, and are coupled to electrodes that contact the myocardium for sensing the heart's electrical signals and for delivering stimulation to the heart in accordance with various therapies. Cardiac rhythm management devices may deliver low energy electrical pace pulses timed to assist the heart in producing a contractile rhythm that maintains cardiac pumping efficiency appropriate to meet the metabolic requirements of the patient.

While transvenous lead delivery is appropriate for many patients that experience adverse synchronization conditions, placing the leads is typically a difficult and time consuming process requiring highly specialized training. Lead placement is often accomplished by an iterative trial and error process, which may result in non-optimum placement.

Typically, the clinician must manipulate the lead to the desired site, remove the lead positioning stylet, insert a fixation stylet, and then connect electrical clips to the lead to make measurements with a pacing system analyzer. If the clinician is not satisfied with the results given by the pacing system analyzer, the process must be reversed and repeated with a new lead position. It is not uncommon for a clinician to manipulate the lead three or more times before a suitable location is found.

SUMMARY OF THE INVENTION

The present invention is directed to cardiac lead implantation systems and methods of lead implantation. A lead implantation system in accordance with embodiments of the present invention includes an electronics arrangement having a user interface. A coupler assembly is provided with the electronics arrangement, and includes a coupler body configured to detachably grasp an outer surface of the cardiac lead. The coupler body supports a plurality of electrical contacts configured to detachably couple with electrical contacts of a cardiac lead.

Embodiments of a lead implantation system in accordance with the present invention include a cable having a proximal end coupled to the electronics arrangement and a distal end extending from the housing and coupled to the coupler body. Electrical conductors in the cable connect the electronics arrangement to the plurality of electrical contacts in the coupler assembly.

The user interface includes an output device configured to provide a user perceivable output indicative of sensed cardiac parameters, such as one or both of cardiac signal amplitude and lead electrode impedance. The user interface may include an audio output device configured to broadcast user-perceivable audio output indicative of one or both of cardiac signal amplitude and lead electrode impedance. The user interface may optionally, or additionally, include a visual output device configured to produce user-perceivable visual output indicative of one or both of cardiac signal amplitude and lead electrode impedance. Examples of visual output devices include LED display arrangements and graphical displays.

The coupler body may have, for example, a clamshell hinge configured to engage the outer surface of the cardiac lead in a closed configuration and to release engagement with the outer surface of the cardiac lead in an open configuration. The clamshell hinge has an axial length, and the clamshell hinge may extend along at least a majority of the axial length. Hinging the clamshell is only one method of connecting the coupler body together. Other connection mechanisms, such as snap fitting or other connection arrangements may be utilized without departing from the scope of embodiments of the present invention. The coupler body may include one or more protrusions, such as ribs, fingers, or the like, configured to contact the outer surface of the cardiac lead.

The coupler body includes an inner passage configured to accommodate a cardiac lead when the coupler body detachably grasps the outer surface of the cardiac lead. Cardiac leads may include an open lumen for placement by a stylet. The coupler body includes an inner passage configured to provide access to the open lumen of the cardiac lead while the coupler body detachably grasps the outer surface of the cardiac lead. The cable and/or coupler body may be sterilizable.

The electronics arrangement may include an external connector interface for facilitating connection between the electronics arrangement and an external system, such as an electrophysiology recording system. The electronics arrangement may include energy delivery circuitry that produces a stimulation signal deliverable to cardiac tissue via the lead electrodes. The stimulation signal may include a signal having an energy insufficient to effect capture, such as an AC signal having a frequency in the kilohertz or megahertz range. The electronics arrangement may optionally or additionally include impedance detection circuitry and/or cardiac activity detection circuitry. The electronics arrangement may include a low-pass filter configured to remove high-frequency components of a cardiac activity signal sensed by the electrode arrangement. The housing of the electronics arrangement may include a power source defining a sole source of power for the electronics arrangement.

Embodiments of the present invention are directed to methods of lead implantation involving advancing a cardiac lead into proximity with a patient's heart, and contacting cardiac tissue with an electrode arrangement of the cardiac lead to locate a suitable implant location. Sensing of one or more cardiac parameters is accomplished via the electrode arrangement. An audible representation of the one or more sensed cardiac parameters is produced, the audible representation varying as the electrode arrangement is moved relative to the cardiac tissue.

Stimulation energy may be delivered to the cardiac tissue via the electrode arrangement, wherein at least one sensed cardiac parameter from the one or more cardiac parameters is responsive to the stimulation energy. Contacting, sensing, and producing may be performed simultaneously. The variations in the audible representation may be indicative of variations in implant location suitability, such as by sensing an impedance of the electrode arrangement.

Sensing the one or more cardiac parameters may involve sensing a depolarization event and determining a signal amplitude associated with the depolarization event. The audible representation may include a plurality of audible representations associated with a corresponding plurality of cardiac parameters, such as an audible tone representative of electrode arrangement impedance and a pulsed audible tone representative of depolarization events and their amplitudes.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
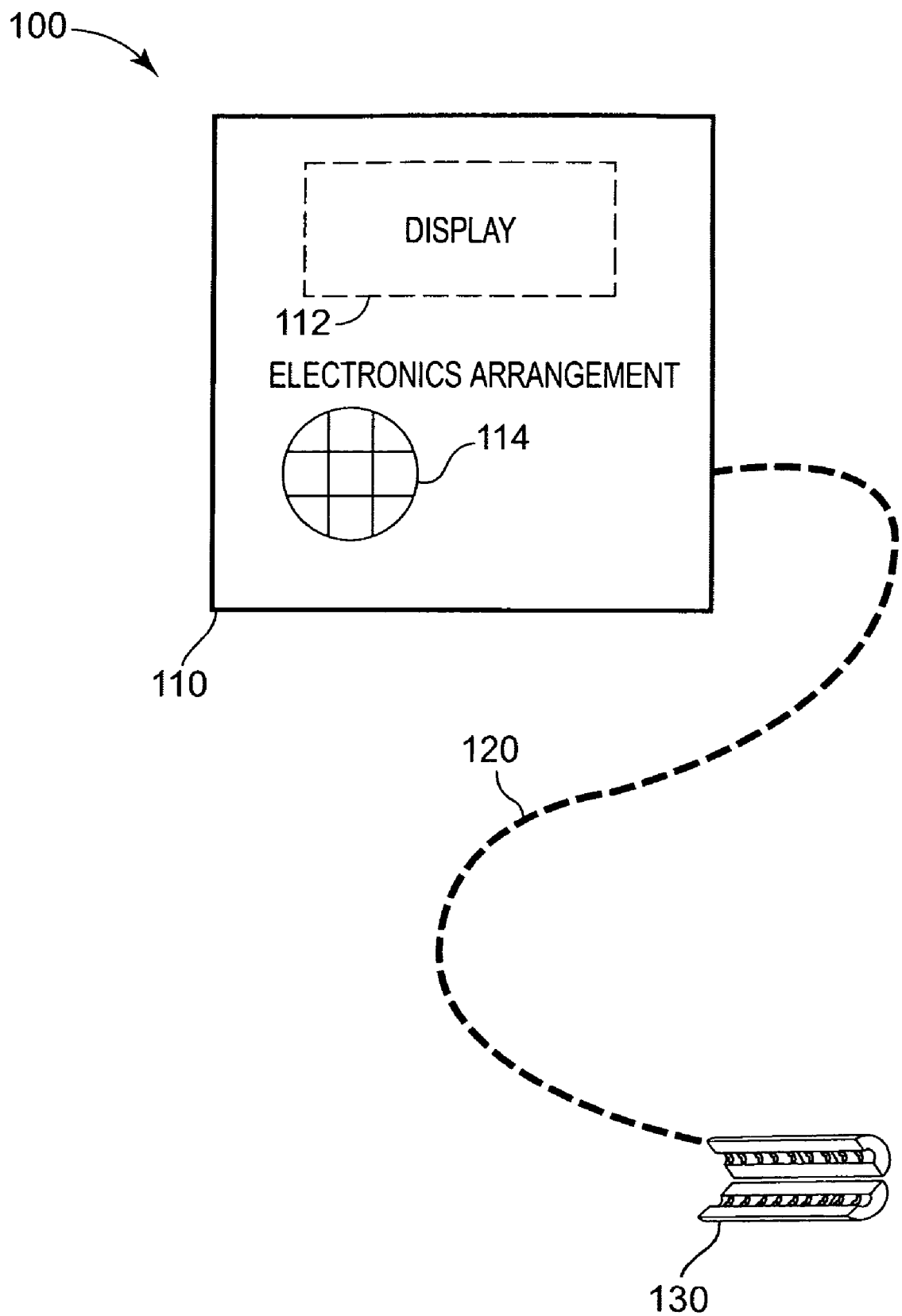
FIG. 1 is an embodiment of a block diagram of a cardiac lead implantation system in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

Methods and articles of manufacture employing a lead implantation system in accordance with embodiments of the present invention may incorporate one or more of the features, structures, methods, or combinations thereof described herein below. For example, a lead implantation system or method may be implemented to include one or more of the features and/or processes described below. It is intended that such a device or method need not include all of the features and functions described herein, but may be implemented to include one or more selected features and functions that provide for unique structures and/or functionality.

FIG. 1 is a block diagram of a cardiac lead implantation system 100 in accordance with an embodiment of the present invention. The system 100 includes an electronics arrangement 110, a coupler assembly 130, and may optionally include a cable 120 connecting the coupler assembly 130 to the electronics arrangement 110. The system 100 may optionally incorporate the electronics arrangement 110 into the coupler assembly 130, eliminating the cable 120 (see, for example, FIG. 2B).

The electronics arrangement 110 includes a user perceivable output device, such as a display 112 and/or an audio output 114, examples of which include a speaker or headphone connector. The display 112 may be any device that can visually represent a signal value, such as an LED display, such as a bar graph, an LCD display, or a video output signal capable of being displayed on a monitor or CRT.

Figure 2A:
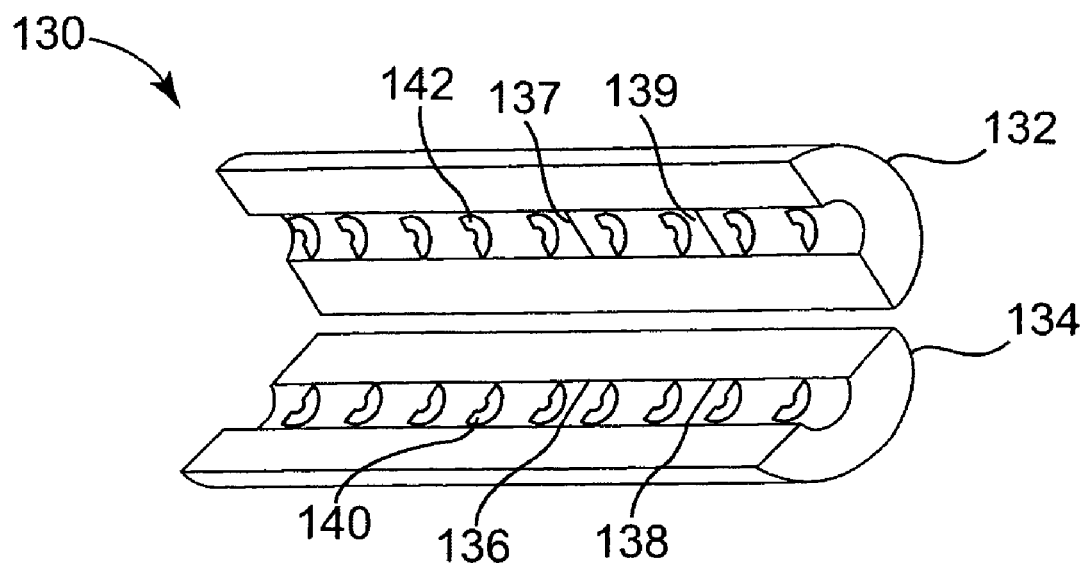
FIG. 2A illustrates an embodiment of a lead coupling assembly in an open configuration in accordance with the present invention.

FIG. 2A illustrates the coupler assembly 130 in an open configuration in accordance with an embodiment of the present invention. As is illustrated in FIG. 2A, the coupler assembly 130 includes a first shell 132 and a second shell 134 that may be arranged in a clamshell fashion, to engage the outside of a standard cardiac lead using a clamshell hinge arrangement. It is understood that other engagement or attachment arrangements may be employed.

One or both of the first shell 132 and the second shell 134 may include electrical contacts configured to couple with the contacts of a cardiac lead. For example, the first shell 132 is illustrated as incorporating a first electrical contact 137 and a second electrical contact 139. The second shell 134 is illustrated as incorporating a third electrical contact 136 and a fourth electrical contact 138. As is illustrated in FIG. 2A, the first electrical contact 137 may oppose the third electrical contact 136, and the second electrical contact 139 may oppose the fourth electrical contact 138, such that clamping the coupler assembly 130 around a cardiac lead effects electrical connection between the electronics arrangement 110 and the electrodes and/or sensors of the cardiac lead. The coupler assembly 130 may further include one or more deformable ridges 140, 142 configured to grasp the outside of a cardiac lead firmly, but without causing damage.

Figure 2B:
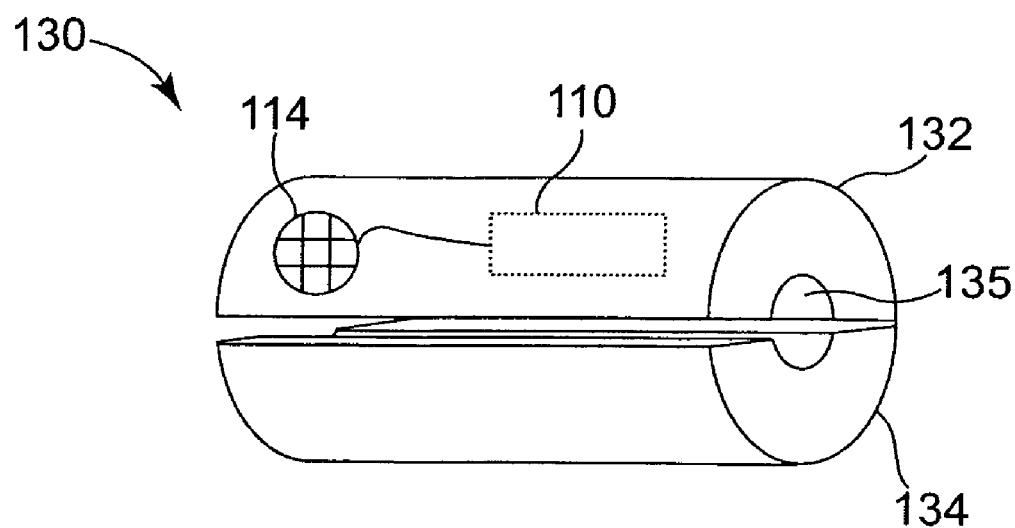
FIG. 2B illustrates a lead coupling assembly in a closed configuration in accordance with an embodiment of the present invention that includes circuitry with the coupler assembly.

FIG. 2B illustrates the coupler assembly 130 in a closed configuration in accordance with another embodiment of the present invention, with the electronics arrangement 110 included with the coupler assembly 130. The coupler assembly 130 is illustrated in a closed position, having a bore 135 configured to releasably grasp a cardiac lead, while still providing access to the lumen of the cardiac lead, for example, for use of a stylet or other guide arrangement. The coupler assembly 130 illustrated in FIG. 2B may include contacts such as are illustrated in the coupler assembly 130 of FIG. 2A. The coupler assembly 130 illustrated in FIG. 2A may have a bore 135 configured to releasably grasp a cardiac lead, while still providing access to the lumen of the cardiac lead, such as is illustrated in the coupler assembly 130 of FIG. 2B.

The coupler assembly 130 is illustrated in FIG. 2B as including the electronics arrangement 110 with the coupler assembly 130. The speaker 114 may also be included with the coupler assembly 130, and/or may be provided remotely from the coupler assembly 130 and connected wirelessly using a short-range wireless communication interface conforming to a known communications standard, such as the Bluetooth or the IEEE 802 standards. In one configuration, for example, the electronics arrangement 110 of the coupler assembly 130 may incorporate a wireless communication interface, and the speaker 114 and/or other user interface devices/systems (e.g., display, graphical output device) may provide user perceivable output remotely of the coupler assembly 130 via wireless communication with the electronics arrangement 110. The wireless communication may be uni-directional or bi-directional as between the coupler assembly 130 and externally situated devices/systems.

Figure 3:
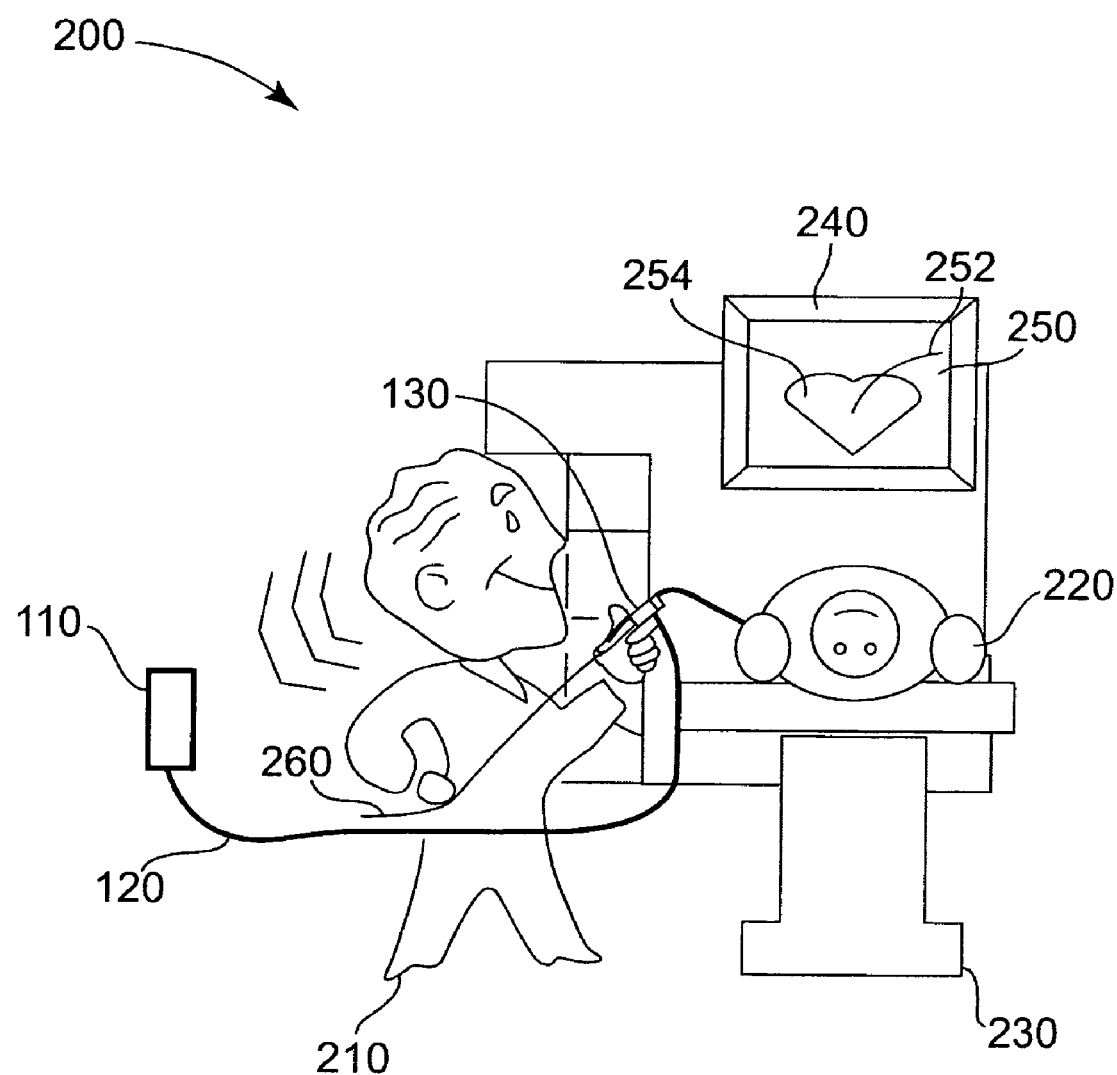
FIG. 3 is an illustration of a cardiac lead implantation system in use by a clinician in accordance with methods of the present invention.

FIG. 3 is an illustration of a clinical setting 200, where the cardiac lead implantation system 100 (Illustrated in FIG. 1) is in use by a clinician 210 in accordance with methods of the present invention. The clinician 210 is depicted as watching a fluoroscope 240, with an image 250 of a heart 254 as a lead 252 is inserted into a heart chamber. The clinician 210 is guiding the lead 252 using a stylet 260 running through the bore 135 (Illustrated in FIG. 2B) of the coupler assembly 130. The coupler assembly 130 is here illustrated with the cable 120 attaching the coupler assembly 130 to the electronics arrangement 110. In alternate embodiments, the coupler assembly 130 may incorporate the electronics arrangement 110 with the coupler assembly 130, and/or may be equipped with a short-range wireless communication interface. The clinician is listening to the electronics arrangement 110 as the lead 252 is advanced to the heart 254 and in contact with the heart 254.

As the clinician 210 is guiding the lead 252, the electronics arrangement 110 senses, via an electrode arrangement of the lead 252, one or more cardiac parameters such as electrical impedance. The electronics arrangement 110 may also provide electrical stimulation to the heart 254 via the lead 252, and sense any electrophysiological response from the stimulation. Energy delivery circuitry may be provided in the electronics arrangement 110 that produces a high-frequency AC stimulation signal deliverable to cardiac tissue via one or more lead electrodes of the lead 252. For example, the electronics arrangement 110 may produce an AC signal having a frequency in the kilohertz or megahertz range. The electronics arrangement 110 may also detect cardiac cycles, and examine cardiac waveforms, such as depolarization events (e.g. R-waves and/or P-waves), to determine cardiac rhythms, capture, and/or other events. A power source, such as a battery, may be included in the electronics arrangement 110, and may define a sole source of power for the electronics arrangement 110.

An embodiment of a user perceivable output from the electronics arrangement 110 may include, for example, an electrocardiogram signal that may be visually displayed, either on the display 112 (Illustrated in FIG. 1) of the electronics arrangement 110, on the coupler assembly 130, and/or on the fluoroscope 240. For example, the electronics arrangement 110 may provide a signal, having electrocardiogram information sensed from the cardiac lead 252, that may be displayed near and/or overlaid on the fluoroscope 240 image, to assist the clinician 210 with implant site decision making.

The electronics arrangement 110 uses the sensed parameter(s) to provide a user perceivable output providing information to the clinician 210 about the sensed parameter(s). For example, the electronics arrangement 110 may provide an audible tone and/or pulse repetition that may be altered according to the sensed parameter. As a non-limiting example, the frequency of a continuous tone may be increased as the electrical impedance of the lead's electrodes decreases or increases. The lower electrical impedance may indicate a preferred implantation site for the lead 252. Other user perceivable audio variations include changes of tone, tone bursts with varying tone pulse widths and/or pulse repetition rates, and combinations of these audible characteristics.

Figure 4:
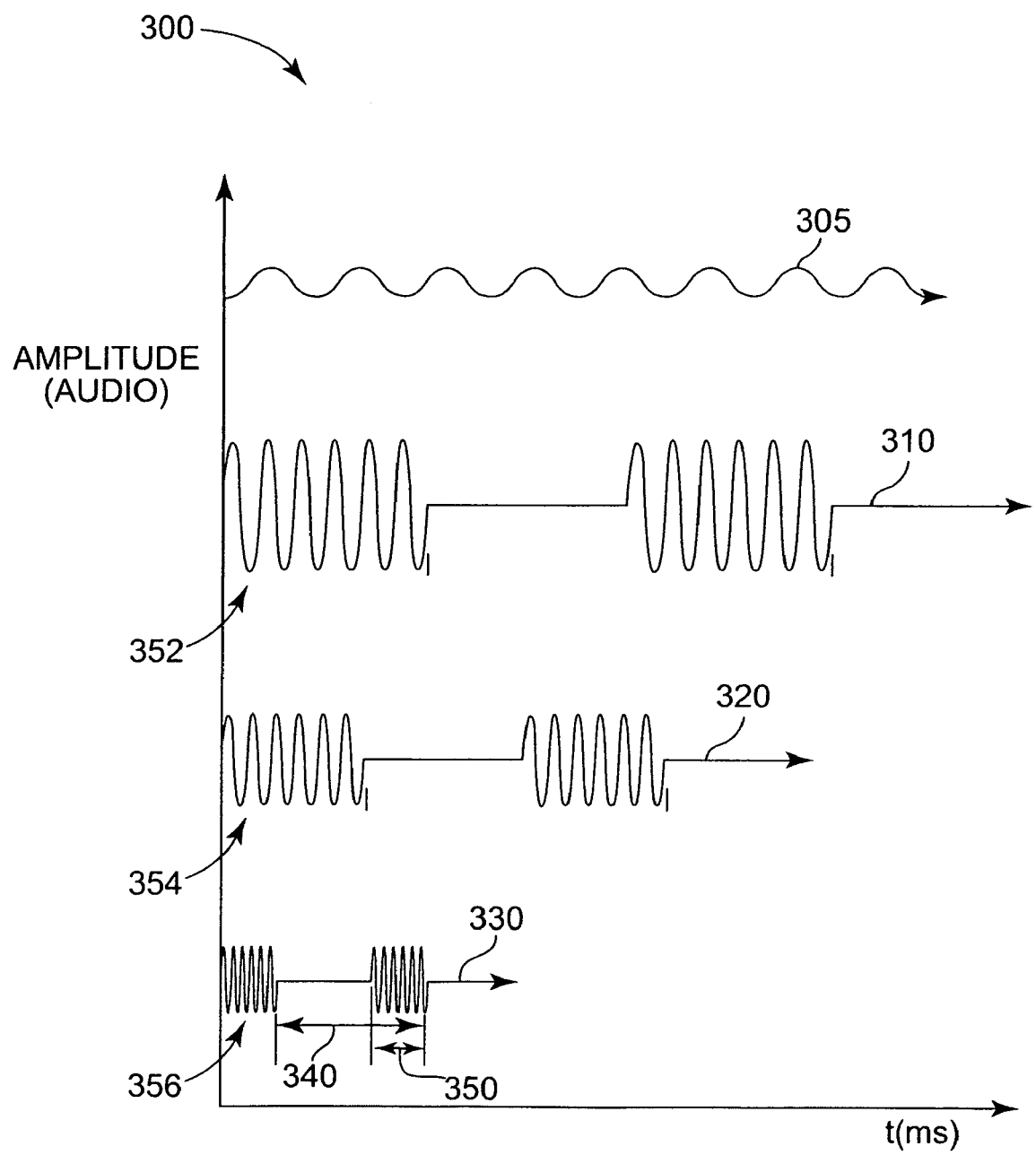
FIG. 4 is a graph of audio tone-bursts useful in accordance with embodiments of the present invention.

FIG. 4 is a graph 300 of audio tone-bursts useful in accordance with embodiments of the present invention. The graph 300 has time indicated on the abscissa, and signal amplitude indicated on the ordinate. A first continuous audio signal 305, a second audio signal 310, a third audio signal 320, and a fourth audio signal 330 are illustrated on the graph 300. The first audio signal 305 is a continuous tone, whose pitch may be varied as a measured parameter varies. The second audio signal 310 includes a low pitch tone burst 352, the third audio signal 320 includes a medium pitch tone burst 354, and the fourth audio signal 330 includes a high pitch tone burst 356.

The fourth audio signal 330 is designated with a pulse repetition rate 340 and a tone burst duty cycle 350. As is illustrated by the signals 305, 310, 320, 330 in graph 300, possible audio aspects useful to provide information to a user include the signal amplitudes, pulse repetition rates, duty cycles, and pitches. For example, a user perceivable audio signal may be provided with altered amplitude, altered duty cycle, altered pulse repetition rate, and altered pitch to designate a change in one or more sensed parameters. The audio signal may simultaneously provide information about up to four sensed parameters or combinations of parameters using all four audio aspects, each designating a different sensed parameter or combination of parameters.

As an example embodiment, the pitch of the continuous audio signal 305 may be decreased as the impedance decreases, so that the clinician is maneuvering the lead 252 to attain the lowest continuous pitch possible. The second variable pitch tone burst audio signal 310 may be added to the first continuous audio signal 305. Each variable pitch tone pulse in 305 occurs when a QRS cardiac signal is detected by the electronics arrangement, and the pitch is determined by the QRS amplitude. The clinician 210 is then maneuvering the lead 252 to attain the lowest continuous pitch possible and the highest pulsed tone pitch possible, to a suitable implantation site in the heart 254 in this example.

Referring now to FIGS. 3 and 4, as an example, the two parameters of impedance and QRS peak amplitude of a cardiac signal may be of interest to the clinician 210. The audio output signal amplitude produced by the electronics arrangement 110 may be kept constant, at a level pleasing to the clinician 210. The pitch of the audio signal may be decreased as the impedance decreases, so that the clinician is maneuvering the lead 252 to attain the lowest pitch possible. The duty cycle may be kept constant, but the pulse repetition rate may be increased as the QRS peak amplitude increases, indicating increased cardiac response to a pacing pulse. The clinician 252 is then maneuvering the lead 252 to attain the lowest pitch possible and the highest pulse repetition rate possible, to locate a suitable implantation site in the heart 254 in this example. The clinician may be permitted to select and/or change the feedback characteristics and/or parameters, such that the feedback information is delivered in a form most useful to the clinician.

Figure 5:
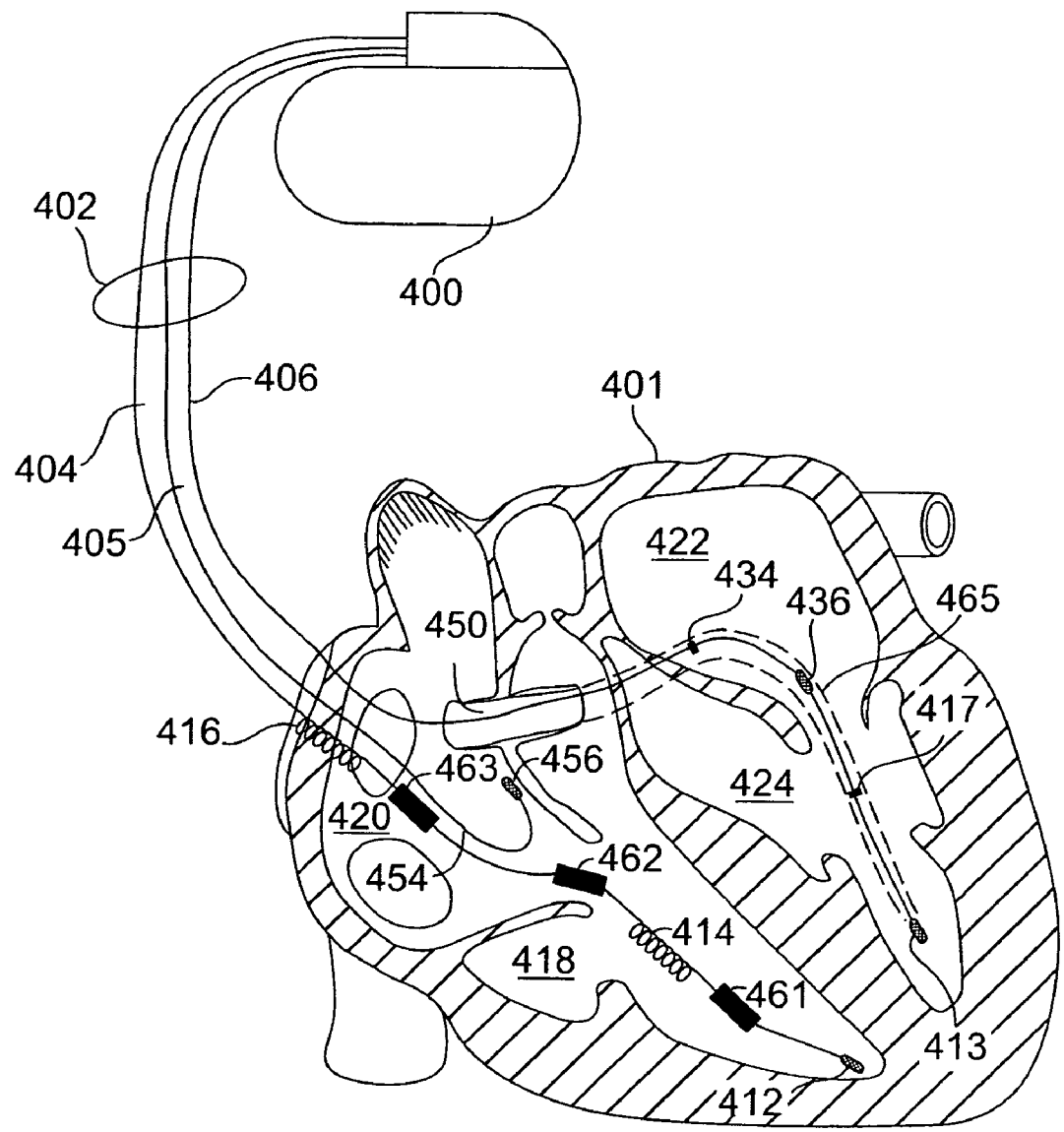
FIG. 5 is an illustration of an implantable cardiac device including a lead assembly shown implanted in a sectional view of a heart, the lead assembly implantable using a lead implantation system in accordance with an embodiment of the present invention.

Referring to FIG. 5, there is shown a body implantable device that represents one of several types of devices with implantable leads that may benefit from a lead implantation system in accordance with embodiments of the present invention. For example, a patient internal medical device (PIMD) 400, illustrated in FIG. 5 as a pacemaker/defibrillator, may be representative of all or part of a pacemaker, defibrillator, cardioverter, cardiac monitor, or re-synchronization device (e.g., multichamber or multisite device). Accordingly, the lead implantation methodologies of the present invention may be useful for implanting leads used in a wide variety of implantable medical devices that sense cardiac activity.

The implantable device illustrated in FIG. 5 is an embodiment of the PIMD 400 including an implantable pacemaker/defibrillator electrically and physically coupled to an intracardiac lead system 402. The intracardiac lead system 402 is implanted in a human body with portions of the intracardiac lead system 402 inserted into a heart 401. Electrodes of the intracardiac lead system 402 may be used to detect and analyze cardiac signals produced by the heart 401 and to provide stimulation and/or therapy energy to the heart 401 under predetermined conditions, to treat cardiac arrhythmias of the heart 401.

The PIMD 400 depicted in FIG. 5 is a multi-chamber device, capable of sensing signals from one or more of the right and left atria 420, 422 and the right and left ventricles 418, 424 of the heart 401 and providing pacing pulses to one or more of the right and left atria 420, 422 and the right and left ventricles 418, 424. Low energy pacing pulses may be delivered to the heart 401 to regulate the heartbeat or maintain a cardiac rhythm, for example. In a configuration that includes cardioversion/defibrillation capabilities, high-energy pulses may also be delivered to the heart 401 if an arrhythmia is detected that requires cardioversion or defibrillation.

The intracardiac lead system 402 includes a right ventricular lead system 404, a right atrial lead system 405, and a left atrial/ventricular lead system 406. The right ventricular lead system 404 includes an RV-tip pace/sense electrode 412, an RV-coil electrode 414, and one or more electrodes 461, 462, 463 suitable for measuring transthoracic impedance. In one arrangement, impedance sense and drive electrodes 461, 462, 463 are configured as ring electrodes. The impedance drive electrode 461 may be located, for example, in the right ventricle 418. The impedance sense electrode 462 may be located in the right atrium 420. Alternatively or additionally, an impedance sense electrode 463 may be located in the superior right atrium 420 or near the right atrium 420 within the superior vena cava.

The RV-tip electrode 412 is positioned at an appropriate location within the right ventricle 418 for pacing the right ventricle 418 and sensing cardiac activity in the right ventricle 418. The right ventricular lead system may also include one or more defibrillation electrodes 414, 416, positioned, for example, in the right ventricle 418 and the superior vena cava, respectively.

The atrial lead system 405 includes A-tip and A-ring cardiac pace/sense electrodes 456, 454. In the configuration of FIG. 5, the intracardiac lead system 402 is positioned within the heart 401, with a portion of the atrial lead system 405 extending into the right atrium 420. The A-tip and A-ring electrodes 456, 454 are positioned at an appropriate location within the right atrium 420 for pacing the right atrium 420 and sensing cardiac activity in the right atrium 420.

The lead system 402 illustrated in FIG. 5 also includes a left atrial/left ventricular lead system 406. The left atrial/left ventricular lead system 406 may include, one or more electrodes 434, 436, 417, 413 positioned within a coronary vein 465 of the heart 401. Additionally, or alternatively, one or more electrodes may be positioned in a middle cardiac vein, a left posterior vein, a left marginal vein, a great cardiac vein or an anterior vein.

The left atrial/left ventricular lead system 406 may include one or more endocardial pace/sense leads that are advanced through the superior vena cava (SVC), the right atrium 420, the valve of the coronary sinus, and the coronary sinus 450 to locate the LA-tip 436, LA-ring 434, LV-tip 413 and LV-ring 417 electrodes at appropriate locations adjacent to the left atrium 422 and left ventricle 424, respectively. In one example, lead placement involves creating an opening in a percutaneous access vessel, such as the left subclavian or left cephalic vein. For example, the lead system 402 may be guided into the right atrium 420 of the heart via the superior vena cava.

From the right atrium 420, the left atrial/left ventricular lead system 406 is deployed into the coronary sinus ostium, the opening of the coronary sinus 450. The left atrial/left ventricular lead system 406 is guided through the coronary sinus 450 to a coronary vein of the left ventricle 424. This vein is used as an access pathway for leads to reach the surfaces of the left atrium 422 and the left ventricle 424 which are not directly accessible from the right side of the heart. Lead placement for the left atrial/left ventricular lead system 406 may be achieved via subclavian vein access. For example, a preformed guiding catheter may be used for insertion of the LV and LA electrodes 413, 417, 436, 434 adjacent the left ventricle 424 and left atrium 422, respectively.

Lead placement for the left atrial/left ventricular lead system 406 may be achieved via the subclavian vein access and a preformed guiding catheter for insertion of the LV and LA electrodes 413, 417, 436, 434 adjacent the left ventricle 424 and left atrium 422, respectively. In one configuration, the left atrial/left ventricular lead system 406 is implemented as a single-pass lead. It is understood that the descriptions in the preceding paragraphs with regard to LV-tip 413 and LV-ring 417 electrodes are equally applicable to a lead configuration employing distal and proximal LV ring electrodes (with no LV-tip electrode).

Additional configurations of sensing, pacing and defibrillation electrodes may be included in the intracardiac lead system 402 to allow for various sensing, pacing, and defibrillation capabilities of multiple heart chambers. In other configurations, the intracardiac lead system 402 may have only a single lead with electrodes positioned in the right atrium or the right ventricle to implement single chamber cardiac pacing. In yet other embodiments, the intracardiac lead system 402 may not include the left atrial/left ventricular lead 406 and may support pacing and sensing of the right atrium and right ventricle only. Any intracardiac lead and electrode arrangements and configurations may be implanted within the scope of the present system in accordance with embodiments of the invention.

Figure 6:
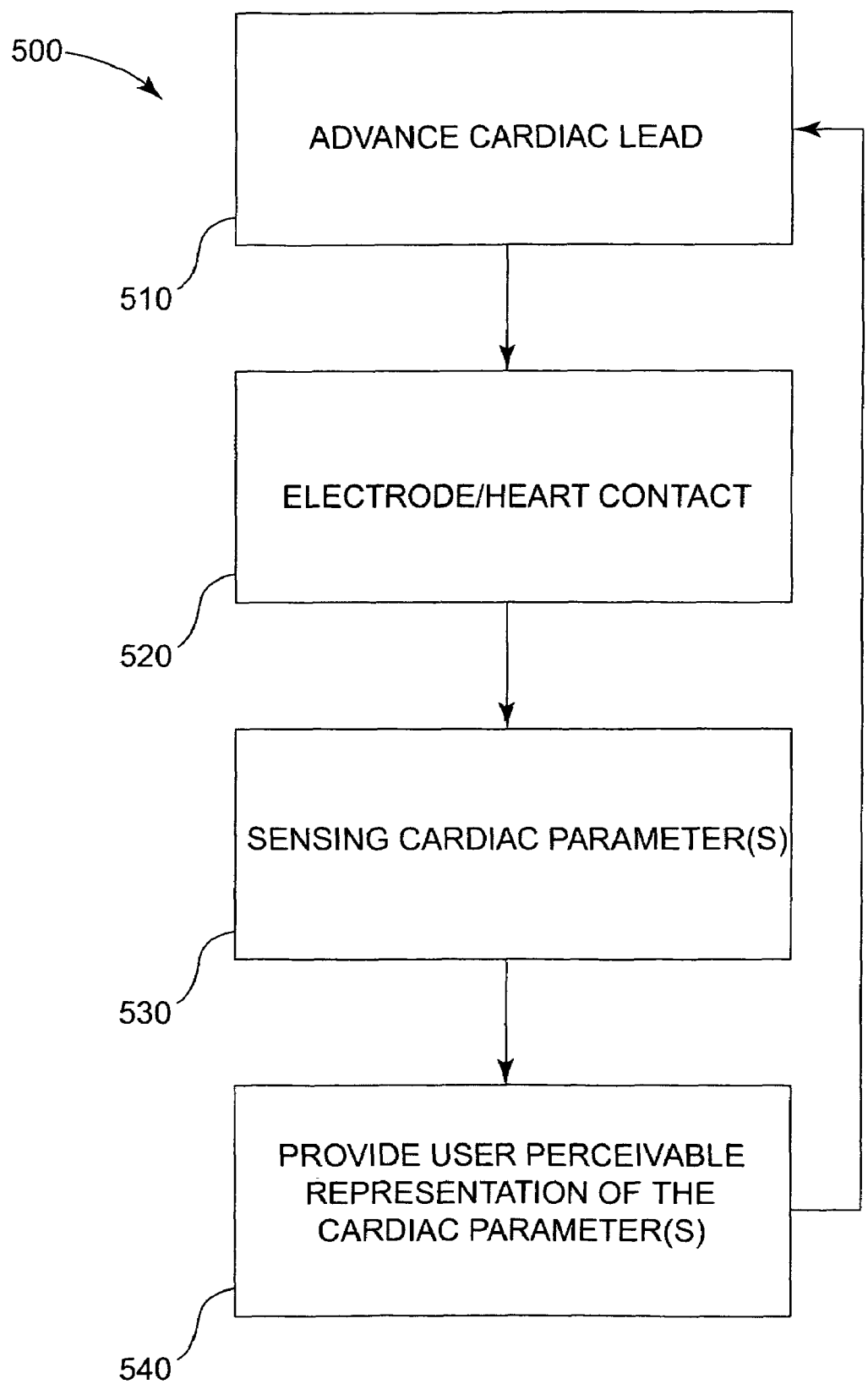
FIG. 6 is a flow chart of a method of lead implantation in accordance with embodiments of the present invention.

FIG. 6 is a flow chart of a method 500 of lead implantation in accordance with embodiments of the present invention. The method 500 involves advancing a cardiac lead 510, for example within a ventricle of a patient's heart. As the lead is advanced 510, an electrode on the lead makes contact 520 with the myocardium inside the heart's ventricle. The contact 520 provides an electrical pathway for sensing cardiac parameters 530, such as measuring the electrode's impedance at its current location, measuring electrophysiological signals, sensing tissue perfusion, or other desired sensing.

The sensed parameter(s) 530 are converted from their measured state into a user perceivable representation 540, such as using a visual display and/or an audible cue. As is indicated in FIG. 6, the method 500 may be performed continuously as the lead is advanced and moved to new locations, as the clinician searches for an acceptable or optimal placement location. For example, if electrode contact 520 is broken with the myocardium, the sensed parameter 530 may exhibit an out-of-range status, and the user perceivable representation may be an audible cue indicating loss of contact. Sensed impedance with contact may be represented by tone bursts with a pulse repetition rate, and loss of contact may be represented by a continuous tone, for example.

Figure 7:
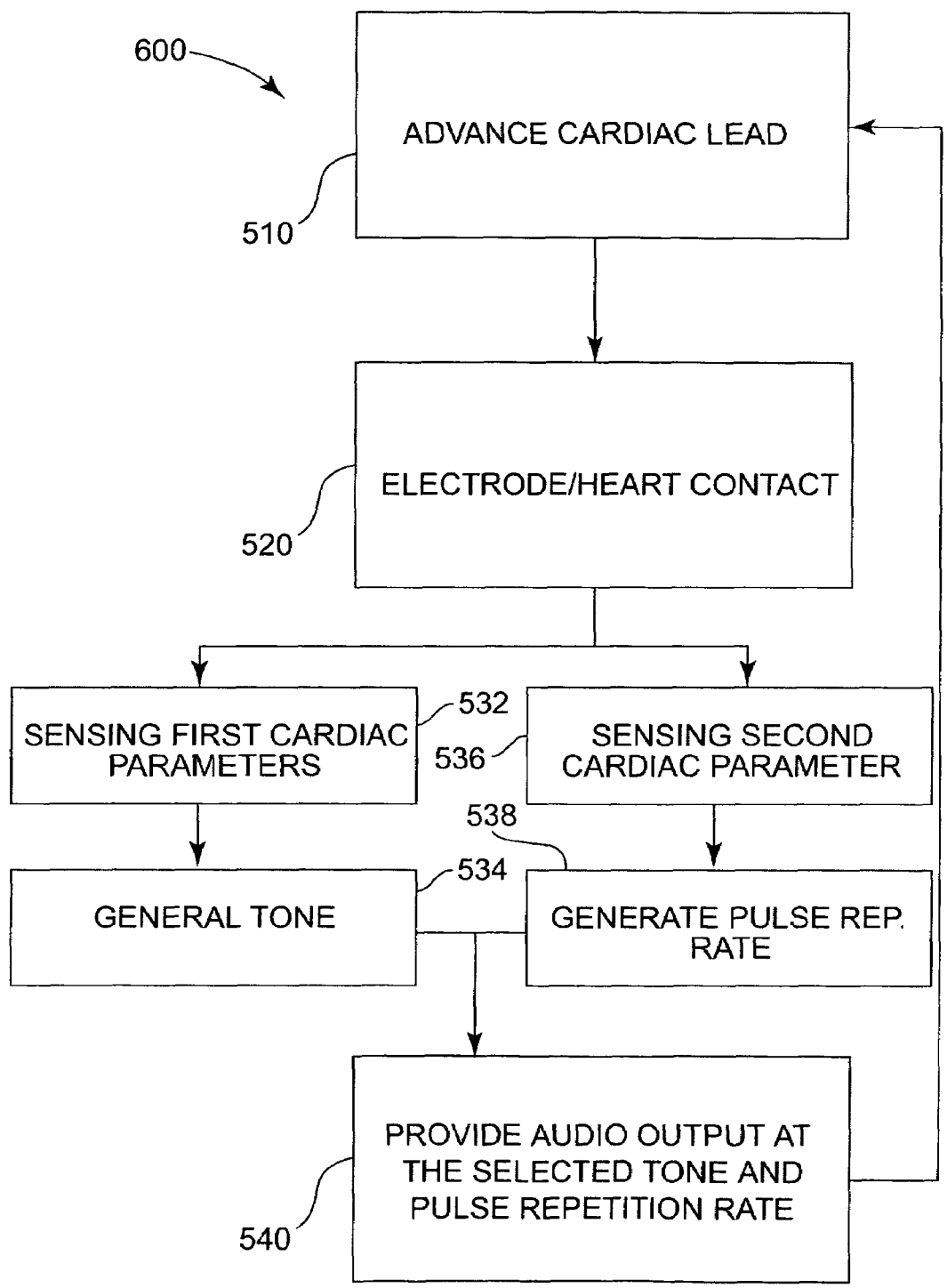
FIG. 7 is a flow chart of another method of lead implantation in accordance with embodiments of the present invention.

FIG. 7 is a flow chart of a method 600 of lead implantation in accordance with embodiments of the present invention, providing user feedback for two sensed parameters in this example. In the example illustrated in FIG. 7, the process of sensing cardiac parameters 530 (Illustrated in FIG. 6) is broken into a two parameter sensing variation. In the embodiment illustrated in FIG. 7, a first cardiac parameter 532 is sensed, and a tone 534 is generated to represent the first cardiac parameter 532. Concurrently, a second cardiac parameter 536 is sensed and a variable pitch tone burst 538 is generated to represent the second sensed parameter 536. The user perceivable output 540 is then the combined tone 534 and variable pitch tone burst 538, which simultaneously provides the user with information about both parameters as the lead is advanced 510 and manipulated.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A patient-external system for coupling to an implantable cardiac lead having two or more lead electrodes, comprising:
    a coupler assembly, comprising:
        a coupler body configured to detachably grasp an outer surface of the cardiac lead, the coupler body comprising a clamshell hinge configured to forcibly engage the outer surface of the cardiac lead in a closed configuration and to release forcible engagement with the outer surface of the cardiac lead in an open configuration; and
        a plurality of electrical contacts supported by the coupler body, the plurality of electrical contacts configured to detachably couple with electrical contacts of the cardiac lead; and
    an electronics arrangement coupled to the coupler body, the electronics arrangement comprising a user interface configured to provide one or both of user perceivable audio and visual output.

2. The system of claim 1, wherein the electronics arrangement is disposed in or on the coupler body.

3. The system of claim 1, comprising:
    a cable comprising a proximal end coupled to the electronics arrangement and a distal end extending from the housing and coupled to the coupler body; and
    electrical conductors in the cable connecting the electronics arrangement to the plurality of electrical contacts.

4. The system of claim 1, wherein the user interface comprises an audio output device configured to broadcast user-perceivable audio output indicative of one or both of cardiac signal amplitude and lead electrode impedance.

5. The system of claim 1, wherein the user interface comprises a visual output device configured to produce user-perceivable visual output indicative of one or both of cardiac signal amplitude and lead electrode impedance.

6. The system of claim 5, wherein the visual output device comprises a graphical display of an electrocardiogram signal sensed by the electrode.

7. The system of claim 1, wherein the coupler body comprises a plurality of protrusions configured to forcibly contact the outer surface of the cardiac lead.

8. The system of claim 1, wherein the coupler body comprises an inner passage configured to accommodate the cardiac lead when the coupler body detachably grasps the outer surface of the cardiac lead.

9. The system of claim 1, wherein the cardiac lead comprises an open lumen, and the coupler body comprises an inner passage configured to provide access to the open lumen of the cardiac lead while the coupler body detachably grasps the outer surface of the cardiac lead.

10. The system of claim 1, wherein the coupler body is sterilizable.

11. The system of claim 1, wherein the electronics arrangement comprises an external connector interface for facilitating connection between the electronics arrangement and an external system.

12. The system of claim 1, wherein the electronics arrangement comprises energy delivery circuitry that produces a stimulation signal deliverable to cardiac tissue via the two or more lead electrodes.

13. The system of claim 1, wherein the electronics arrangement comprises impedance detection circuitry.

14. The system of claim 1, wherein the electronics arrangement comprises cardiac activity detection circuitry.

15. The system of claim 1, wherein the coupler body comprises a power source, the power source defining a sole source of power for the electronics arrangement.

16. A patient-external system for coupling to an implantable cardiac lead having two or more lead electrodes, comprising:
    a coupler assembly, comprising:
        a coupler body configured to detachably grasp an outer surface of the cardiac lead, the coupler body comprising a plurality of protrusions configured to forcibly contact the outer surface of the cardiac lead; and a plurality of electrical contacts supported by the coupler body, the plurality of electrical contacts configured to detachably couple with electrical contacts of the cardiac lead; and an electronics arrangement coupled to the coupler body, the electronics arrangement comprising a user interface configured to provide one or both of user perceivable audio and visible output.

17. The system of claim 16, wherein the electronics arrangement is disposed in or on the coupler body.

18. The system of claim 16, comprising:
a cable comprising a proximal end coupled to the electronics arrangement and a distal end extending from the housing and coupled to the coupler body; and
electrical conductors in the cable connecting the electronics arrangement to the plurality of electrical contacts.

19. The system of claim 16, wherein the user interface comprises an audio output device configured to broadcast user-perceivable audio output indicative of one or both of cardiac signal amplitude and lead electrode impedance.

20. The system of claim 16, wherein the user interface comprises a visual output device configured to produce user-perceivable visual output indicative of one or both of cardiac signal amplitude and lead electrode impedance.

21. The system of claim 20, wherein the visual output device comprises a graphical display of an electrocardiogram signal sensed by the electrode.

22. The system of claim 16, wherein the coupler body comprises an inner passage configured to accommodate the cardiac lead when the coupler body detachably grasps the outer surface of the cardiac lead.

23. The system of claim 16, wherein the cardiac lead comprises an open lumen, and the coupler body comprises an inner passage configured to provide access to the open lumen of the cardiac lead while the coupler body detachably grasps the outer surface of the cardiac lead.

24. The system of claim 16, wherein the coupler body is sterilizable.

25. The system of claim 16, wherein the electronics arrangement comprises an external connector interface for facilitating connection between the electronics arrangement and an external system.

26. The system of claim 16, wherein the electronics arrangement comprises energy delivery circuitry that produces a stimulation signal deliverable to cardiac tissue via the two or more lead electrodes.

27. The system of claim 16, wherein the electronics arrangement comprises impedance detection circuitry.

28. The system of claim 16, wherein the electronics arrangement comprises cardiac activity detection circuitry.

29. The system of claim 16, wherein the coupler body comprises a power source, the power source defining a sole source of power for the electronics arrangement.

* * * * *